United States Patent [19]
Posner

[11] Patent Number: 5,817,692
[45] Date of Patent: Oct. 6, 1998

[54] ENDOPEROXIDES USEFUL AS ANTIPARASITIC AGENTS

[75] Inventor: Gary H. Posner, Baltimore, Md.

[73] Assignee: The Johns Hopkins University, Baltimore, Md.

[21] Appl. No.: 701,423

[22] Filed: Aug. 22, 1996

Related U.S. Application Data

[63] Continuation-in-part of Ser. No. 562,275, Nov. 22, 1995, Pat. No. 5,672,624.
[51] Int. Cl.$^6$ ............... A61K 31/335; C07D 321/10; C07D 323/04
[52] U.S. Cl. .............. 514/450; 514/452; 549/350; 549/363
[58] Field of Search ................ 549/350, 363; 514/450, 452

[56] References Cited

U.S. PATENT DOCUMENTS

| | | |
|---|---|---|
| 4,977,174 | 12/1990 | Stein . |
| 5,057,501 | 10/1991 | Thornfeldt . |
| 5,578,637 | 11/1996 | Lai . |

OTHER PUBLICATIONS

Posner et al., Tet. Lett., 37(6), 815–818, Feb. (1996).
Posner et al., ibid., 37(40), 7225–7228, Sep. (1996).
Jiang et al., Antimalarial Activity of Mefloquine and Qinghaosu, The Lancet, 7 Aug. 1982, pp. 285–288.
Bruce–Chwatt, Qinghaosu: a new antimalarial, British Medical Journal, vol. 284, 13 Mar. 1982, pp. 767–768.
Klayman, Qinghaos.u (Artemisinin): An Antimalarial Drug from China, Science, vol. 228, 31 May 1985, pp. 1049–1055.
Miyashi et al., Evidence for a Chair Cyclohexane 1,4–Radical Cation . . . of 2,5–Diaryl–11,5–hexadienes, J. Am. Chem. Soc., 1988. 110. pp. 3676–3677.
Miyashi et al., Photoinduced electronic–transfer reactions of the cope and related systems, Pure & Appl. Chem., 1990. vol. 62, No. 8, pp. 1531–1538.
Takahashi et al., Electron–Transfer . . . 2,6–Diarylhepta–1, 6–dienes, Tetrahedron Letters, 1994, vol. 35, No. 23, pp. 3953–3956.
Cope et al., Cyclic Polyolefins . . . Cyclooctatetra–enes, J. Am. Chem. Soc. (1955) vol. 77, pp. 4939–4940.
Desjardins, et al., Quantitative Assessment . . . Technique, Antimicrobial Agents and Chemotherapy. Dec 1979. pp. 710–718.
Milhous et al., In Vitro Activities . . . Antimalarial Drugs, Antimicrobial Agents and Chemotherapy. Apr. 1985, pp. 525–530.
Carmichael et al., Evaluation of a . . . Testing, Cancer Research 47, Feb. 15, 1987, pp. 936–942.
Fraser et al., Is Uracil . . . Treatment?, Biochemical & Biophysical Research Communications, vol. 135, No. 3, 1986, Mar. 28, 1986, pp. 886–893.
Posner, et al., Further Evidence . . . Like Artemisinin, J. of Medicinal Chemistry, vol. 38, No. 13, pp. 2273–2275, 1995.
Hudson, Atovaquone —A Novel Broad–spectrum Anti–infective Drug, Parasitology Today, vol. 9, No. 2, 1993, pp. 66–68.
Schmid et al., Total Synthesis of Qinghaosu, J. Am. Chem. Soc., 1983, 105, pp. 624–625.

*Primary Examiner*—Johann Richter
*Assistant Examiner*—Laura L. Stockton
*Attorney, Agent, or Firm*—Cushman Darby & Cushman IP Group of Pillsbury Madison & Sutro

[57] ABSTRACT

The present invention relates to novel biologically-active organic peroxides and to novel uses of both known and new organic peroxides. More specifically, this invention details organic endoperoxides having antiparasitic activity, methods for their preparation and methods for treating malaria and cerebral toxoplasmic encephalitis with the organic endoperoxides.

22 Claims, No Drawings

ENDOPEROXIDES USEFUL AS ANTIPARASITIC AGENTS

This application is a continuation-in-part of pending U.S. application Ser. No. 08/562,275, filed Nov. 22, 1995, now U.S. Pat. No. 5,672,624.

The invention described and claimed herein was made in part under a grant from the National Institutes of Health, NIH-AI-34885. The Government has certain rights in the invention.

BACKGROUND OF THE INVENTION

1. Field of the Invention

The present invention relates to novel biologically-active organic peroxides and to novel uses of both known and new organic peroxides. More specifically, this invention details organic endoperoxides having antiparasitic activity, methods for their preparation and methods for treating malaria and cerebral toxoplasmic encephalitis with the organic endoperoxides.

2. Description of the Related Art

The trioxane drug artemisinin is an active anti-malarial constituent of the herb *Artemisia annua* L., Compositae. The herb has been known in China for almost 2000 years. Artemisinin was first isolated in 1972 and shown to be a sesquiterpene lactone with a peroxide moiety (1). The molecular structure was first reported in 1983 (2) and is shown in the following formula:

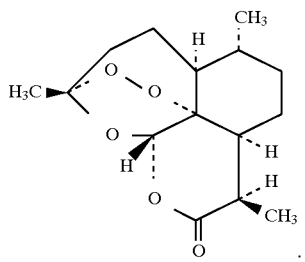

Several investigators have reported on the anti-malarial activity of artemisinin (3–5). Several reviews of the chemistry, pharmacology and clinical applications of artemisinin have been reported (6–8).

We have used our understanding of molecular mechanisms of action to design and synthesize a series of structurally simple endoperoxides patterned after artemisinin, some of which have previously been reported (9–11). Biological evaluation of these synthetic organic peroxides has surprisingly shown some of them to be potent and relatively nontoxic antiparasitic agents with considerable activity against not only malaria but also against cerebral toxoplasmic encephalitis caused by *Toxoplasma gondii*.

SUMMARY OF THE INVENTION

It is an object of the present invention to provide compounds and methods for treating parasitic infections such as malaria and cerebral toxoplasmic encephalitis and infections caused by *Cryptosporidium parvum*. Saturated and unsaturated bicyclic endoperoxides have been found to be extremely effective when used for this purpose.

In one embodiment of the invention, saturated bicyclo (3,2,2) endoperoxide compounds are provided of the formula:

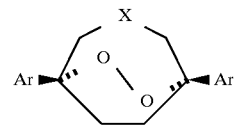

wherein Ar is phenyl and X is selected from the group consisting of:

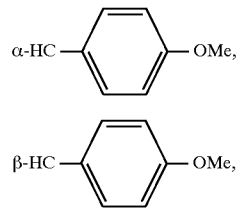

$NSO_2R$, wherein R represents an alkyl or aryl group,

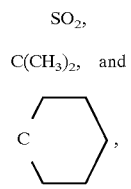

Another embodiment of the invention includes saturated bicyclic compounds of formula

wherein n is 1 or 2 and R and R' are independently selected from the group consisting of H, OH, $OSiMe_2Bu$-t, $CH_2OSiMe_2Bu$-t, $CH_2OH$, $CH_2F$, $OCH_3$, $CH_2OCH_2CONH_2$ and F.

Still another embodiment of the invention includes compounds of the formula

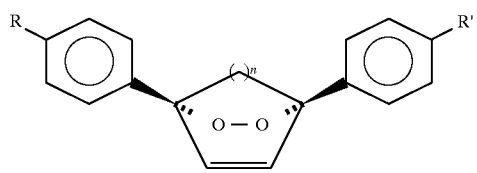

wherein n is 1, 2, 3, or 4; and R and R' are independently selected from the group consisting of H, $CH_3$, F and p-$PhCH_2OCH_2PhF$-p.

A preferred embodiment of the above formula is unsaturated bicyclic endoperoxide compounds of the formula:

wherein n is 3.

In another embodiment of the invention, compounds of the invention can be represented by the formula:

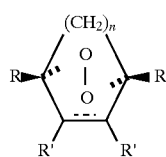

wherein n is 1–4 (preferably 2);

R is a substituted or unsubstituted aryl group; a substituted or unsubstituted heteroaryl group; a substituted or unsubstituted straight chain or branched alkyl ($C_1$–$C_6$) (substituents in each instance including 1 or more or a combination of aryl, heteroaryl, halogen, sulfur, oxygen, nitrogen groups); and R' is H; a substituted or unsubstituted aryl group; a substituted or unsubstituted heteroaryl group; a substituted or unsubstituted ($C_1$–$C_6$) alkyl (substituents in each instance including 1 or more or a combination of aryl, heteroaryl, halogen, sulfur, oxygen, nitrogen groups). Compounds of this formula wherein R' represents a methyl or phenyl group and R represents an aryl, substituted aryl, heteroaryl or substituted heteroaryl group. In one preferred compound of this embodiment R is phenyl and R' is methyl; in another preferred compound R is 3-quinolyl and R' is hydrogen.

The present invention also relates to a method for treating parasitic infections comprising the step of administering an organic endoperoxide to an individual afflicted with a parasitic infection, wherein the organic peroxide is selected from the group consisting of:

a) a compound of the formula:

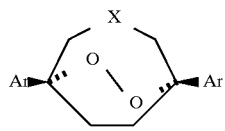

wherein Ar is selected from the group consisting of Ph, p-MeOPh, and p-FPh and X is selected from the group consisting of:

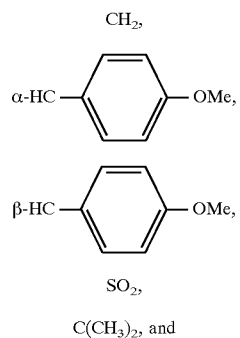

$C(CH_3)_2$, and

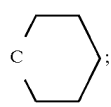

b) a compound of the formula:

wherein n is 1, 2, 3 or 4;

c) a compound of the formula:

d) a compound of the formula:

wherein n is 1 or 2 and R and R' are independently selected from the group consisting of H, OH, $OSiMe_2Bu$-t, $CH_2OSiMe_2Bu$-t, $CH_2OH$, $CH_2F$, $OCH_3$, $CH_2OCH_2CONH_2$ and F; a e) a compound of the formula:

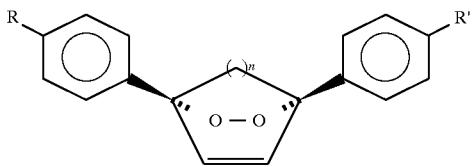

wherein n is 1, 2, 3, or 4; and R and R' are independently selected from the group consisting of H, $CH_3$, F and p-$PhCH_2OCH_2PhF$-p.

Treatment with compounds represented by the formula:

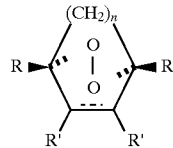

where

R is a substituted or unsubstituted aryl group; a substituted or unsubstituted heteroaryl group; a substituted or unsubstituted straight chain or branched alkyl ($C_1$–$C_6$) (substituents in each instance including 1 or more or a combination of aryl, heteroaryl, halogen, sulfur, oxygen, nitrogen groups); and R' is H; a substituted or unsubstituted aryl group; a substituted or unsubstituted heteroaryl group; a substituted or unsubstituted ($C_1$–$C_6$) alkyl (substituents in each instance including 1 or more or a combination of aryl, heteroaryl, halogen, sulfur, oxygen, nitrogen groups) is also included in the invention.

The therapeutic methods of the invention are particularly useful for the treatment of malaria and cerebral toxoplasmic encephalitis, and should also be useful for infections caused by *Crytosporidium parvum*.

Effective therapeutic dosages of the compounds will vary but can be readily determined by persons of ordinary skill in the medical arts using routine experimentation. It is expected that the compounds of the present invention will be administered to humans as pharmaceutical agents in dosages similar to those which are effective for artemisinin. The required dose for a given individual or infection will vary, but can be determined by ordinarily skilled practitioners using routine methods. Preferred dosages will be in the range of about 0.1–100 mg/kg per day, more preferably about 1–25 mg/kg. The compounds may be administered via methods well known in the pharmaceutical and medical arts, which include, but are not limited to oral, parenteral, topical, and respiratory (inhalation) routes, most preferably oral. Pharmaceutical preparations may contain suitable carriers or diluents. Means of determining suitable carriers and diluents are well known in the pharmaceutical arts.

DETAILED DESCRIPTION OF THE INVENTION

As mention above, the present invention relates to novel organic endoperoxides having antiparasitic activity, methods for their preparation and methods for treating parasitic infections such as malaria and cerebral toxoplasmic encephalitis with the organic endoperoxides. A detailed description for the methods of preparation of the synthetic organic endoperoxides and for the testing of the biological activity of the compounds follows:

1. PREPARATION OF THE ENDOPEROXIDES

The organic endoperoxides of the present invention were prepared as follows. Compounds of the formula:

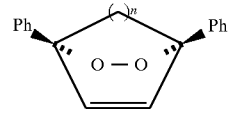

wherein Ar is selected from the group consisting of Ph, p-MeOPh and p-FPh, and X is $CH_2$, were prepared according to the method of Takahashi et al. (11).

The compound of the formula:

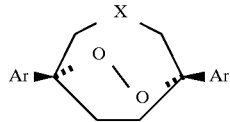

wherein n is 1 was prepared according to the method of Kuhn (12).

The compound of the formula:

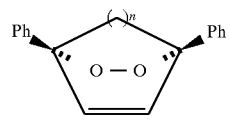

wherein n is 2 was prepared according to the method of Schenck et al. (13).

The compound of the formula:

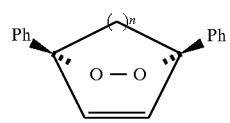

wherein n is 3 was prepared according to the method of Rigaudy et al. (14).

Bicyclo[3.2.2]C-5-p-methoxyphenyl diphenyl peroxides (2α and 2β) of the formula:

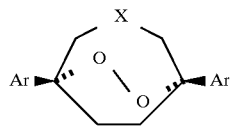

wherein Ar is Ph and X is

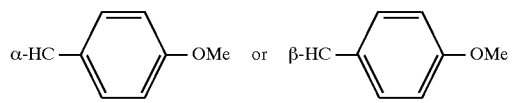

were prepared according to the following procedures.

GENERAL. Tetrahydrofuran (THF) and diethyl ether ($Et_2O$) were distilled from benzophenone ketyl prior to use. Methylene chloride ($CH_2Cl_2$) and triethylamine ($NEt_3$) were distilled from calcium hydride prior to use. Commercially available anhydrous solvents were used in other instances. Unless otherwise noted, all reagents were purchased from Aldrich Chemical Co. (Milwaukee, Wis.) and were used as received without further purification. FT-IR spectra were recorded using a Perkin-Elmer Model 1600 FT-IR spectrophotometer. The $^1H$ and $^{13}C$ NMR spectra were recorded on a Varian XL-400 spectrometer operating 400 MHz and 100 MHz, respectively. Chemical shifts are reported in parts per million (ppm, δ) downfield from tetramethylsilane. Splitting patterns are described as singlet (s), doublet (d), triplet (t), quartet (q), multiplet (m), etc. Low resolution mass spectra (LRMS) and High resolution mass spectra (HRMS) were obtained on VG Instruments 70-S spectrometer run at 70 eV for electronic ionization (EI) or with ammonia ($NH_3$) as a carrier for chemical ionization (CI). High performance liquid chromatography (HPLC) was performed by a Rainin HPLX gradient system. Column chromatography was performed by Silica 60 (70–230 mesh, Merck) or florisil (200 mesh, Aldrich). The reaction vessels were usually oven-dried overnight. Reaction yields are not optimized.

PERODIDES 2α AND 2β.

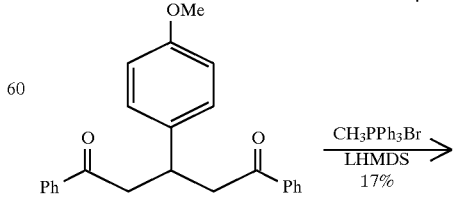

1

-continued
PERODIDES 2α AND 2β.

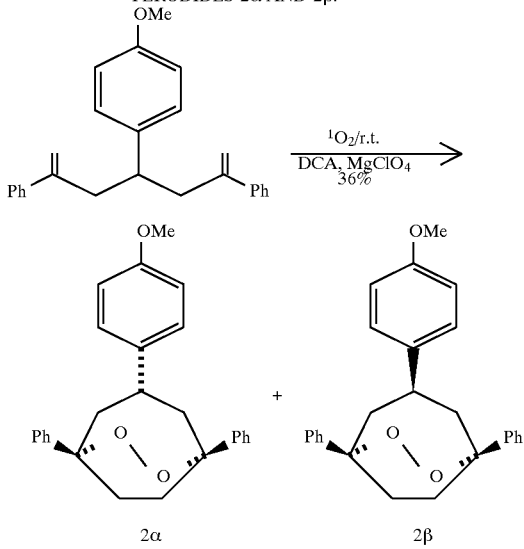

Step 1: An oven-dried round bottom flask charged with commercial pre-dried methyltriphenylphosphonium bromide (3.99 g, 11.2 mmol) and dry THF (20 ml) was cooled down to −78° C. under argon atmosphere. To the solution was added lithium bis(trimethylsilyl)amide (LHMDS; 1M in THF, 14 ml, 14.0 mmol) over 3 min. The resultant yellow ylide solution was stirred at −78° C. for 10 min, then allowed to warm to room temperature and stirred for 1.5 hr. After cooling down again to −78° C., the reaction mixture was treated with commercial diketone (448 mg, 1.25 mmol) in dry THF (5 mL) via a cannula over 5 min. After being stirred at −78° C. for 20 min, the reaction mixture was slowly warmed up to room temperature over 4 hr, stirred for 26 hr at room temperature and then cooled down to 0° C., quenched with warer (10 ml) at 0° C. and diluted with ether (10 ml). The organic layer was separated, and the aqueous layer was extracted twice with ether (10 ml×2). The combined organic layer was washed with brine solution (20 ml), and dried over anhydrous magnesium sulfate, filtered, and concentrated under reduced pressure to yield a crude product which was purified by silica gel column chromatography using 1:99 ethyl acetate:hexane to afford the corresponding diene (74.5 mg, 17%) as colorless oil.

Step 2: An oven-dried 125 ml three necked round-bottomed flask, fitted with magnetic stir-bar, gas inlet and outlet, was charged with the diene (93.4 mg, 0.26 mmol), dicyanoanthracene (DCA; 3 mg), and anhydrous acetonitrile (25 ml). Dry oxygen (flow rate: ca. 1 ml/s) was bubbled to this solution at room temperature for 30 min. Magnesium perchlorate (590 mg, 2.64 mmol) was added into the flask, and oxygen was continuously bubbled through the reaction mixture at room temperature for 2 hr under UV irradiation using a medium-pressure mercury lamp as UV source. The resultant solution was then diluted with water (20 ml) and ether (10 ml), the organic layer was separated, and the aqueous layer was extracted twice with ether (10 ml×2). The combined organic layer was washed with brine solution (20 ml), and dried over anhydrous magnesium sulfate, filtered, and concentrated under reduced pressure to yield a crude product which was purified by silica gel column chromatography using 1:99 ethyl acetate:hexane to afford the corresponding peroxides 2 (36.6 mg, 36%), which were separated by HPLC to give 2α (16.3 mg) and 2β (19.2 mg) both as white solids.

2α: m.p.: 163°–164° C.; FTIR (CHCl$_3$, cm$^{-1}$): 2954, 2931, 2872, 2849, 1611, 1511, 1490, 1467, 1443, 1302, 1249, 1210, 1179, 1032; $^1$H NMR (CDCl$_3$, 400 MHz) δ 7.46–7.42 (m, 4H), 7.36–7.31 (m, 4H), 7.26–7.23 (m, 4H), 6.86–6.83 (m, 2H), 3.95 (m, 1H), 3.78 (s, 3H), 2.70–2.64 (m, 2H), 2.53–2.38 (m, 6H); $^{13}$C NMR (CDCl$_3$, 100 MHz) δ 158.05, 146.89, 137.81, 128.32, 128.21, 127.17, 124.26, 113.93, 80.70, 55.29, 49.81, 38.46, 32.99; LRMS (EI, 70 eV, rel intensity) 386 (M, 1), 354 (M—O$_2$, 1), 239 (18) 237 (11), 159 (11), 143 (13), 129 (13), 121 (14), 104 (100), 91 (20), 77 (40); HRMS calc. for C$_{26}$H$_{26}$O$_3$ (M$^+$) 386.1882, found 386.1878;

2β: m.p.: 202°–203° C.; FTIR (CHCl$_3$, cm$^{-1}$): 3008, 2955, 2932, 2838, 1611, 1513, 1494, 1447, 1462, 1373, 1304, 1248, 1215, 1178, 1037; $_1$H NMR (CDCl$_3$, 400 MHz) δ 7.46–7.41 (m, 4H), 7.32–7.27 (m, 4H), 7.23–7.19 (m, 4H), 6.81–6.78 (m, 2H), 3.73 (s, 3H), 3.44 (m, 1H), 2.60–2.53 (m, 4H), 2.41–2.32 (m, 4H); $_{13}$C NMR (CDCl$_3$, 100 MHz) δ 150.89, 145.88, 137.27, 128.28, 128.24, 124.36, 113.92, 82.27, 55.27, 49.14, 39.23, 29.29; LRMS (EI, 70 eV, rel intensity) 386 (M, 2), 354 (M—O$_2$, 1), 239 (53), 161 (10), 134 (29), 121 (11), 105 (100), 91 (13), 77 (38); HRMS calc. for C$_{26}$H$_{26}$O$_3$ (M$_+$) 386.1882, found 386.1885.

Comparable compounds wherein X is

SO$_2$,

C(CH$_3$)$_2$, or

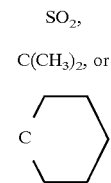

were prepared by comparable procedures.

The compound of the formula:

wherein n is 4 was prepared according to the following procedure. 1,4-Diphenyl-1,3-cyclooctadiene (281 mg, 1.08 mmol), prepared according to the method of Cope et al. (15), was dissolved in dry methylene chloride. To this solution, methylene blue (5 mg) was added. The blue solution was then cooled to −78° C. Dry oxygen was slowly bubbled into the reaction solution under UV irradiation with a medium pressure mercury lamp for 5 hr while the reaction was allowed to warm to room temperature. The reaction mixture was concentrated to give a residue which was subjected to silica gel column chromatography (hexanes/ethyl acetate, 95/5) and further purified by HPLC to give a white solid 26.5 mg, yield 8.4%, m.p. 80.5°–81° C. $^1$H NMR (400 MHz, CDCl$_3$) δ 7.51(4H, ddd, J=7.2, 2.0, 1.6 Hz), 7.36(4H, m), 7.28(2H, tt, J=7.6, 2.0 Hz), 6.35(2H, s), 2.38–2.30(2H, m), 2.15–1.93 (6H, m); $^{13}$C NMR (100 MHz, CDCl$_3$) δ 143.353 (2C), 130.920(2C), 128.371(4C), 127.522(2C), 125.299 (4C), 82.113(2C), 39.738(2C), 25.469(2C); LRMS Calc. for C$_{20}$H$_{20}$O$_2$, 292 (m$^+$), found, 292.

Synthesis of peroxide benzyl alcohol

Peroxide benzyl alcohol was synthesized as summarized in Scheme II.

Scheme II
The Synthesis of peroxide benzyl alcohol 18

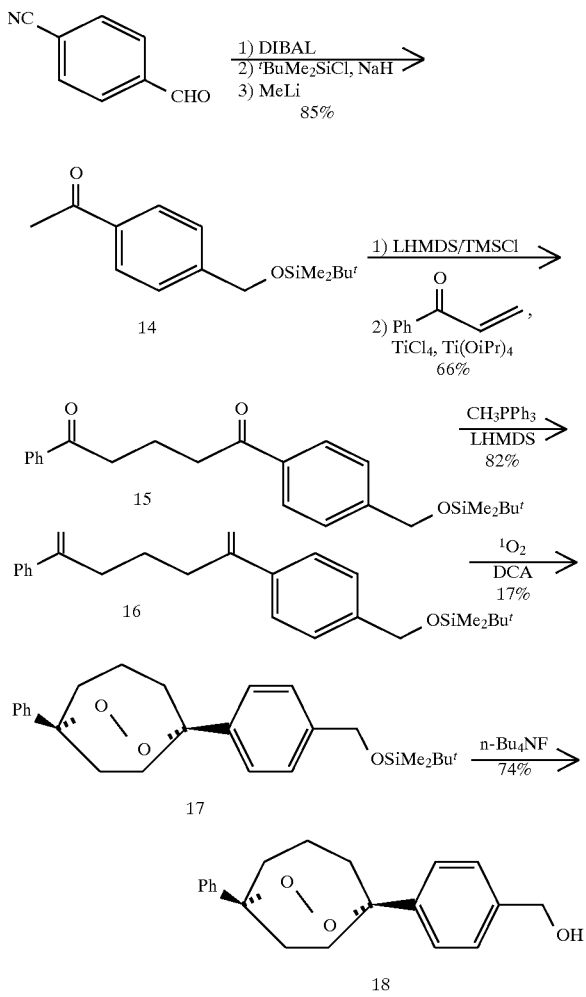

Methyl ketone 14

1) To a solution of p-cyanobenzyl aldehyde (5.03 g, 0.38 mol) in anhydrous ethanol (40 mL) was added sodium borohydride (1.00 g, 0.26 mol) at 0° C. The resulting mixture was stirred for 10 min before warming to room temperature for an additional 15 min, and quenched with 1M HCl until pH was approximately 6. After dilution with water (50 mL) and ether (50 mL) at 0° C., the organic layer was separated and the aqueous layer extracted twice with ether (20 mL×2). The combined organic layer was washed with brine solution (50 mL), and dried over anhydrous magnesium sulfate, filtered, and concentrated under reduced pressure to yield the corresponding benzyl alcohol, which was used in next step without further purification.

2) An oven-dried round bottomed flask charged with NaH (2.28 g, 0.057 mol) in mineral oil was washed with tetrahydrofuran (20 mL×2), and dry THF (100 mL) was added via a syringe under argon atmosphere. A solution of the benzyl alcohol in THF (30 mL) was added to the reaction mixture via a cannula at 0° C. The resulting mixture was stirred at room temperature for 30 min before cannulating in a solution of t-butyldimethylsilyl chloride in THF (30 mL). The reaction mixture was stirred at room temperature for 2 hr, then quenched with water (50 mL) and diluted with ether (50 mL) at 0° C. The organic layer was separated and the aqueous layer was extracted twice with ether (30 mL×2). The combined organic layer was washed with brine solution (50 mL), and then dried over anhydrous magnesium sulfate, filtered, and concentrated under reduced pressure to yield corresponding silyl ether, which was used in the next step without further purification.

3) To a solution of silyl ether in ether (100 mL) was added methyl lithium via a gas-tight syringe at −78° C. under argon atmosphere. The reaction mixture was allowed to warm up to room temperature over 30 min and stirred for addition 2 hr. The mixture was then quenched with water (50 mL) at 0° C., the organic layer was separated and the aqueous layer was extracted twice with ether (50 mL×2). The combined organic layer was washed with brine solution (100 mL), and dried over anhydrous magnesium sulfate, filtered, and concentrated under reduced pressure to yield a crude product, which was purified by silica gel column chromatography using 10:90 ethyl acetate:hexane to afford the corresponding methyl ketone 14 (8.50 g, 85% combined steps) as a colorless oil. 14: FTIR (CHCl$_3$, cm$^{-1}$): 3010, 2956, 2930, 2886, 2858, 1680, 1609, 1575, 1472, 1463, 1412, 1360, 1268, 1095, 1016, 1006, 957; $^1$H NMR (CDCl$_3$, 400 MHz) δ 7.94–7.91 (m, 2H), 7.42–7.39 (m, 2H), 4.79 (s, 2H), 2.59 (s, 3H), 0.95 (s, 9H), 0.11 (s, 6H); $^{13}$C NMR (CDCl$_3$, 100 MHz) δ 197.75, 146.94, 135.81, 128.32, 125.73, 64.40, 26.55, 25.86, 18.34, −5.34; HRMS calc. for C$_{15}$H$_{24}$O$_2$Si (M$^+$) 282.1889 found 282.1894.

Diketone 15

1) To a solution of methyl ketone 9 (2.50 g, 9.5 mmol) in tetrahydrofuran (40 mL) at −78 °C., lithium bis(trimethylsilyl)amide solution (1M, 15.0 mL, 15 mmol) was added via a gas-tight syringe over 2 min under argon atmosphere. The reaction mixture was warmed up to 0° C. and stirred for 10 min, and then treated with trimethylsilyl chloride via a gas-tight syringe (1.9 mL, 15 mmol). After stirring for an additional 2 hr, the mixture was quenched with saturated sodium bicarbonate solution (80 mL) and diluted with hexane 80 mL). The organic layer was separated, and the aqueous layer was extracted twice with hexane (40 mL×2). The combined organic layer was washed with brine solution (100 mL), and dried over anhydrous magnesium sulfate, filtered, and concentrated under reduced pressure to yield a crude product which was purified by silica gel column chromatography using 2:98 ethyl acetate:hexane to afford the corresponding silyl enol ether (ca. 3.4 g, >95%), which was used directly in the next reaction.

2) To a solution of titanium tetrachloride (1M in CH$_2$Cl$_2$, 5.02 mL, 5.0 mmol) in dry methylene chloride (40 mL) titanium isopropoxide (1.20 mL, 4.0 mmol) was slowly added at −78° C. via a gas-tight syringe under argon atmosphere. After being stirred for 10 min, the reaction mixture was slowly treated with a precooled solution containing phenyl vinyl ketone 8 (666 mg, 5.0 mmol) and silyl enol ether from step 1) (3.36, 10 mmol) in dry methylene chloride (30 mL) at −78° C. under argon atmosphere. The resulting mixture was then stirred at −78° C. for 40 min before being quenched with saturated sodium carbonate solution (50 mL) at this temperature and diluted with ether (50 mL). The mixture was passed through Celite to remove solids and the organic layer was separated, and the aqueous layer was extracted twice with ether (40 mL×2). The combined organic layer was washed with brine solution (80 mL), and dried over anhydrous magnesium sulfate, filtered, and concentrated under reduced pressure to yield a crude product which was purified by silica gel column chromatography using 10:90 ethyl acetate:hexane to afford diketone 15 (2.50 g, 66%) as a colorless oil. 15: FTIR (CHCl$_3$, cm$^{-1}$): 3020, 2957, 2931, 2897, 2859, 1682, 1598, 1508, 1472, 1464, 1448, 1411, 1390, 1362, 1268, 1224, 1167, 1120, 1095, 1004; $^1$H NMR (CDCl$_3$, 400 MHz) δ 8.00–7.93 (m, 4H), 7.58 (m, 1H), 7.47–7.39 (m, 4H), 4.79 (3, 2H), 3.11 (t, J=6.8 Hz, 2H), 3.11 (t, J=6.8 Hz, 2H), 2.20 (p, J=6.8 Hz, 2H), 0.95 (s, 9H), 0.11 (s, 6H); $^{13}$C NMR (CDCl$_3$, 100 MHz) δ 199.74, 199.43, 146.40, 136.74, 135.50, 132.96, 128.50, 128.06, 127.98, 64.41, 37.57, 37.52, 25.87, 18.76, 18.33, −5.32; HRMS calc. for C$_{24}$H$_{32}$O$_3$Si (M+H$^+$) 397.2199 found 297.2206.

Diene 16

An oven-dried round bottom flask charged with pre-dried methyltriphenylphosphonium bromide (5.36 g, 15 mmol) and dry THF (30 mL) was cooled down to −78° C. under argon atmosphere. To the solution was added lithium bis (trimethylsilyl)amide (1M in THF, 17.0 mL, 17 mmol) over 3 min. The resultant yellow ylide solution was stirred at −78° C. for 10 min, then allowed to warm to room temperature and stirred for 1.5 hr. After cooling down again to −78° C., the reaction mixture was treated with diketone 15 (1.19 g, 3.0 mmol) in dry THF (10 mL) via a cannula over 5 min. After being stirred at −78° C. for 20 min, the reaction mixture was slowly warmed up to room temperature over 2 hr, stirred for 20 hr at room temperature and then cooled down to 0° C., quenched with water (30 mL) at 0° C. and diluted with ether (20 mL), the organic layer was separated, and the aqueous layer was extracted twice with ether (20 mL×2). The combined organic layer was washed with brine solution (50 mL), and dried over anhydrous magnesium sulfate, filtered, and concentrated under reduced pressure to yield a crude product which was purified by silica gel column chromatography using 1:99 ethyl acetate:hexane to afford the corresponding diene 16 (968 mg, 82%) was a colorless oil. 16: FTIR (CHCl$_3$, cm$^{-1}$): 3014, 2957, 2931, 2859, 1691, 1598, 1509, 1464, 1449, 1410, 1362, 1261, 1167, 1121, 1007, 911; $^1$H NMR (CDCl$_3$, 400 MHz) δ 7.35–7.19 (m, 9H), 5.24 (m, 2H), 5.02–4.98 (m, 2H), 4.70 (s, 2H), 2.50 (t, J=7.2 Hz, 4H), 1.58 (m, 2H); 0.92 (s, 9H), 0.08 (s, 6H); $^{13}$C NMR (CDCl$_3$, 100 MHz) δ 148.16, 147.93, 141.10, 140.46, 139.66, 128.20, 127.23, 126.07, 125.91, 112.42, 112.06, 64.73, 34.79, 34.77, 26.60, 25.98, 18.45, −5.22;

HRMS calc. for C$_{26}$H$_{36}$OSi (M$^+$) 392.2535 found 392.2531.

Peroxide 17

An oven-dried 1 L three necked round-bottomed flask, fitted with magnetic stir-bar, gas inlet and outlet, was charged with the diene 16 (1.01 g, 2.6 mmol), dicyanoanthracene (15 mg), and anhydrous acetonitrile (500 mL). Dry oxygen (flow rate: ca. 1 mL/s) was bubbled to this solution at room temperature for 30 min. Magnesium perchlorate (5.80 mg, 26 mmol) was added to the flask, and oxygen continuously bubbled through the reaction mixture at room temperature for 11 hr under UV irradiation using a medium-pressure mercury lamp as UV source. The reaction mixture was then concentrated under reduced pressure to 200 mL. The resultant solution was diluted with water (200 mL) and ether (200 mL), the organic layer was separated, and the aqueous layer was extracted twice with ether (100 mL×2). The combined organic layer was washed with brine solution (200 mL), and dried over anhydrous magnesium sulfate, filtered, and concentrated under reduced pressure to yield a crude product which was purified by silica gel column chromatography using 1:99 ethyl acetate:hexane to afford the corresponding peroxide 17 (189 mg, 17%) as colorless oil. 17 FTIR (CHCl$_3$, cm$^{-1}$): 3009, 2928, 2856, 1607, 1512, 1462, 1364, 1255, 1174, 1062, 914, 842; $^1$H NMR (CDCl$_3$, 400 MHz) δ 7.45–7.35 (m, 4H), 7.34–7.26 (m, 4H), 7.26–7.20 (m, 1H), 4.71 (s, 2H); 2.42–2.26 (m, 6H), 2.21–2.15 (m, 2H), 2.10–1.97 (m, 1H), 1.93–1.71 (m, 1H), 0.93 (s, 9H), 0.09 (s, 6H); $^{13}$C NMR (CDCl$_3$, 100 MHz) δ 146.38, 144.97, 140.23, 128.21, 127.05, 125.91, 124.33, 124.26, 82.71 (2), 64.65, 40.47 (2),, 29.36, 29.34, 25.96, 21.26, 18.42, −5.24; HRMS calc. for C$_{26}$H$_{36}$O$_3$Si (M+H$^+$) 442.2777 found 442.2773.

Peroxide 18

To a solution of peroxide 17 (216 mg, 0.51 mmol) in dry THF (3 mL) was added freshly-made tetrabutylammonium fluoride (160 mg, 0.61 mmol) in dry THF (2 mL) via a cannula at 0° C. under argon atmosphere. The resulting solution was stirred at 0° C. for 40 min, diluted with water (10 mL) and ether (5 mL) at 0° C. The organic layer was separated, and the aqueous layer was extracted twice with ether (5 mL×2). The combined organic layer was washed with brine solution (5 mL), and dried over anhydrous magnesium sulfate, filtered, and concentrated under reduced pressure to yield a crude product which was separated by Florisil chromatography using 10:90 ethyl acetate:hexane to afford the corresponding peroxide benzyl alcohol 18 (118 mg, 74%) as a white solid. 18: m.p.: 144° C.; FTIR (CHCl$_3$, cm$^{-1}$): 3624, 2919, 2860, 1672, 1661, 1608, 1596, 1461, 1449, 1355, 1267, 1249, 1268, 1037, 914, 836; $^1$H NMR (CDCl$_3$, 400 MHz) δ 7.42–7.38 (m, 4H), 7.33–7.28 (m, 4H), 7.25–7.20 (m, 1H) 4.63 (s, 2H), 2.43–2.21 (m, 6H), 2.21–2.11 (m, 3H), 2.22–1.96 (m, 1H), 1.93–1.80 (m, 1H); $^{13}$C NMR (CDCl$_3$, 100 MHz) δ 145.23, 145.77, 139.67, 128.24, 127.10, 126.89, 124.59, 124.31, 82.78, 82.69, 64.94, 40.45, 40,42, 29.38, 29.23, 21.22; HRMS calc. for C$_{20}$H$_{22}$O$_3$ (M+H$^+$) 328.1913 found 328.1907.

Synthesis of Unsaturated bicyclic endoperoxides

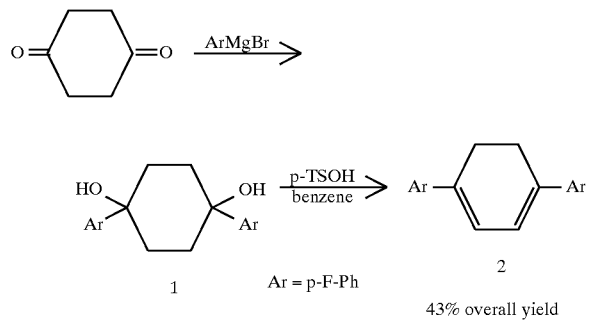

43% overall yield

To a solution of 4-fluorophenyl magnesium bromide (10.5 mL, 2.0M in ethyl ether) in 50 mL of ethyl ether at room temperature, was added a solution of 1,4-cyclohexanedione (0.8 g, 7.1 mmol) in 20 mL of ethyl ether in 30 minutes. The reaction mixture was stirred at room temperature overnight, and quenched by pouring into cold saturated ammonium chloride solution (100 mL). The ether layer was separated, and the aqueous layer was extracted with ethyl acetate (50 mL×3). The combined organic layer was dried (MgSO$_2$), evaporated to give a residue which was chromatographed on a silica gel column (6/4, hexanes/EtOAC) to give diol 1 (1.3 g) which was subjected to the dehydration reaction directly. The diol was dissolved in 60 mL of benzene. p-Toluenesulfonic acid (20 mg) was added to the benzene solution and the resulting reaction mixture was refluxed for 15 minutes while the water formed was removed by a dean-stark separator. The benzene was evaporated and the residue was chromatographed to give diene 2 (0.82 g, yield 43%). $^1$H NMR (400 MHz, CDCl$_3$) δ 7.45–7.42 (4H, m), 7.08–7.00 (4H, m), 6.445 (2H, s), 2.749 (4H, s); $^{13}$C NMR (100.6 MHz, CDCl$_3$) δ 161.99 (2 C, d, J=247.3 Hz), 136.651

(2 C, d, J=3.8 Hz), 134.68 (2 C, s), 126.40 (4 C, d, J=8.4 Hz), 121.2 (2 C, s), 115.27 (4 C, d, J=21.4 Hz), 26.18 (2 C, S)

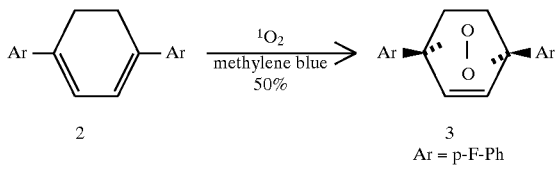

2

3
Ar = p-F-Ph

A solution of 1,4-di-(4-fluorophenyl)-1,3-cyclohexadiene 2 (170 mg) in 50 mL of dry methylene chloride was irradiated with a medium pressure mercury lamp using methylene blue (5 mg) as a sensitizer for three hours at 0° C. while dry oxygen was bubbled into the reaction solution slowly. The reaction mixture was concentrated and the residue was chromatographed on a silica gel column to give peroxide product 3 (95 mg) as a white solid, yield 50% m.p. 152°–153° C. $^1$H NMR (400 MHz, CDCl$_3$) δ 7.52 (4H, ddd, J=8.8, 5.2, 2.4 Hz), 7.12 (4H, m), 6.85 (2H, s), 2.635 (2H, ddd, J=12.0, 4.8, 2.0 Hz), 2.07 (2H, ddd, J=12.0, 4.8, 2.0 Hz); $^{13}$C NMR (100.6 MHz, CDCl$_3$) δ 162.7 (2 C, d, J=247.98 Hz), 136.47 (2 C, s), 134.99 (2 C, d, J=3.02 Hz). 128.15 (4 C, J=8.35 Hz), 115.55 (4 C, d, J=21.4 Hz), 77.96 (2 C, s), 29.29 (2 C, s).

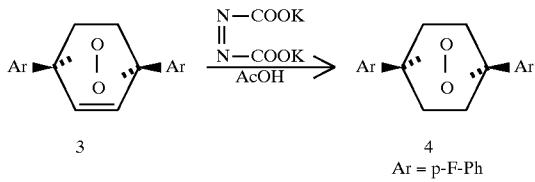

3

4
Ar = p-F-Ph

To a solution of peroxide 3 (20 mg, 0.0667 mmol) in 15 mL methanol, was added 380 mg of potassium azodicarboxylate. Acetic acid (0.24 mL) dissolved in methanol (2 mL) was added dropwise over 30 minutes. After complete addition of the acid, the reaction mixture was stirred for a further 2 hours, then poured into 50 mL of water. The aqueous solution was extracted with ethyl acetate (3×30 mL), and the ethyl acetate layers were combined and washed with saturated sodium bicarbonate solution (30 mL) and water (30 mL). The organic solution was dried (MgSO$_2$) and ethyl acetate was removed by evaporation. 20 mg of product 4 was obtained with spectral properties matching those of the further purified product. Further purification by HPLC (hexanes/ethyl acetate=9/1) yielded a solid, m.p. 208°–209° C. $^1$H NMR (400 MHz, CDCl$_3$) δ 7.41 (4H, ddd, J=8.8, 5.2, 2.4 Hz), 7.05 (4H, m), 2.475 (4H, dd, J=12.0, 4.8 Hz), 2.23 (4H, dd, J=12.0, 4.8 Hz); $^{13}$C NMR (100.6 MHz, CDCl$_3$) δ 162.34 (2 C, d J=247.3 Hz), 137.81 (2 C, d, J=3.0 Hz), 127.04 (4 C, d, J=7.65 Hz), 115.26 (4 C, d, J=21.3 Hz), 77.90 (2 C), 31.52 (4 C).

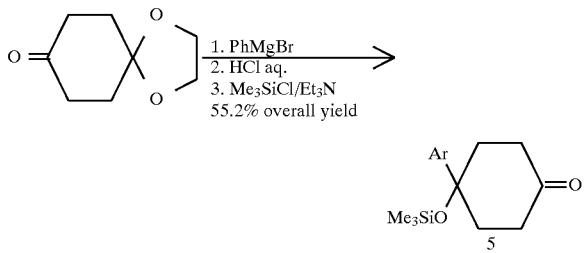

To a solution of 1,4-cyclohexanedione mono-ethylene ketal (6.6 g, 42.3 mmol) in 150 mL of dry ethyl ether at 0° C., was added phenyl magnesium bromide ethyl ether solution (20 mL, 3.0M) over 30 minutes. The reaction mixture was then stirred at room temperature over night. The reaction mixture was poured into 150 mL of cold saturated ammonium chloride water solution. After stirring for 10 minutes, the organic layer was separate and the aqueous solution was extracted with EtOAc (100 mL×3) and the combined organic solution was dried (MgSO$_2$), and evaporated. The residue was chromatographed on a silica gel column to give 9.1 g product (91% yield). This Grignard reaction product (5.0 g, 21.3 mmol) was dissolved in 60 mL of THF, and 5 mL of 2N hydrochloric acid was added. The mixture was stirred at 50° C. overnight. The reaction mixture was cooled to room temperature, diluted with 50 mL of water and neutralized by addition of saturated sodium bicarbonate solution slowly. The mixture was then extracted with ether (100 mL×3) and the combined ether solution was washed with borine (100 mL) and water (100 mL), dried (MgSO$_2$), and evaporated to produce a residue which was chromatographed to give 3.2 g (79%) deprotected product. To a solution of this deprotected product (2.65 g, 13.9 mmol) in 20 mL of dry methylene chloride at 0° C., was added trimethylsilyl chloride (TMSCl, 4.53 g, 42 mmol), triethylamine (4.7 g, 46.5 mmol) and 4-dimethylaminopyridine (DMAP, 50 mg). The reaction mixture was stirred at room temperature overnight. Usual workup and silica gel column chromatography afforded desired product 5 (2.5 g, 76.8%). $^1$H NMR (400 Mhz, CDCl$_3$) δ 7.47 (2 Hm d, J=7.2 Hz), 7.34 (2 H, dd, J=7.2, 7.2 Hz), 7.28 (1H, tdd, J=7.2, 2.0, 1.6 Hz), 2.849 (2H, td, J=13.6, 5.6 Hz), 2.43–2.36 (2,H, m), 2.36–2.29 (2H, m), 2.153 (2H, td, J=13.6, 4.4 Hz). $^{13}$C NMR (100.6 MHz, CDCl$_3$) δ 211.755 (1 C), 145.94 (1 C), 128.18 (2 C), 127.545 (1 C), 125.587 (2 C), 73.996 (1 C), 38.699 (2 C), 347.447 (2 C), 1.892 (3 C).

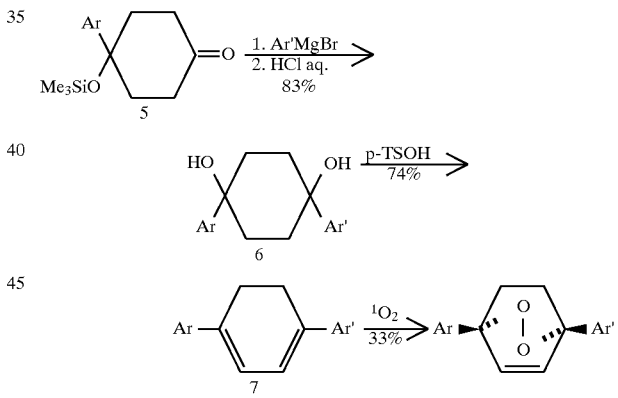

Ar = Ph, Ar' = p-F—Ph

To a solution of ketone 5 (0.55 g, 2.1 mmoL) in 10 mL of ether at room temperature was added 4-fluorophenyl magnesium bromide (2.0 mL, 2.0 Min ether) over 2 minutes. The reaction was stirred at r.t. for a further 30 minutes. The reaction mixture was poured into 50 mL of cold saturated ammonium chloride water solution. The aqueous solution was extracted with EtOAc (50 mL×4) and the combined organic solution was dried (MgSO$_2$), and evaporated. The residue was chromatographed on a silica gel column (hexanes/EtOAc=8/2) to give 0.63 g product which was directly dissolved in 10 mL of THF. To this THF solution was added 1 mL of 2N HCl and the reaction mixture was stirred at r.t. for 30 minutes. Usual workup and silica gel column chromatography (hexanes/EtOAc=1/1) gave diol 6 (0.5 g, yield 83%) in two steps. To a solution of diol 6 (100 mg) in 20 mL of benzene, was added p-toluenesulfonic acid (5 mg) and the resulting mixture was refluxed 10 minutes while the water formed was removed by a dean-stark separator. The benzene was evaporated and the residue was chromatographed to give diene 7 (65 mg, yield 74%). A solution of diene 7 (30.5 mg, 0.122 mmol) in 30 mL of dry methylene chloride was irradiated with a medium pressure mercury lamp using methylene blue (5 mg) as a sensitizer for three hours at 0° C. while dry oxygen was bubbled into the reaction solution slowly. The reaction mixture was concentrated and the residue was chromatographed on a silica gel column to give peroxide product 8 (19 mg, yield 55%). For compound 8: $^1$H NMR (400 MHz, CDCl$_3$) δ 7.55–7.50 (4H, m), 7.45–7.35 (3H, m), 7.14–7.08 (2H, m), 6.886 (1H, d, J=8.4 Hz), 6.831 (1H, d, J=8.4 Hz), 2.68–2.60 (2H, m), 2.06–1.96 (2,H, m); $^{13}$C NMR (100.6 MHz, CDCl$_3$ δ 162.66 (1 C, d, J=248.0 Hz), 139.26 (1 C, s), 136.75 (1 C, s), 136.25 (1 C, s), 135.18 (1 C, d, J=3.1 Hz), 128.58 (2 C, s) 128.50 (1 C, s), 128.14 (2 C, d, J=8.45 Hz), 126.11 (2 C, s), 115.51 (2 C, d, J=21.4 Hz), 78.365 (1 C, s), 77.963 (1 C, s), 29.429 (1 C, s), 29.391 (1 C, s).

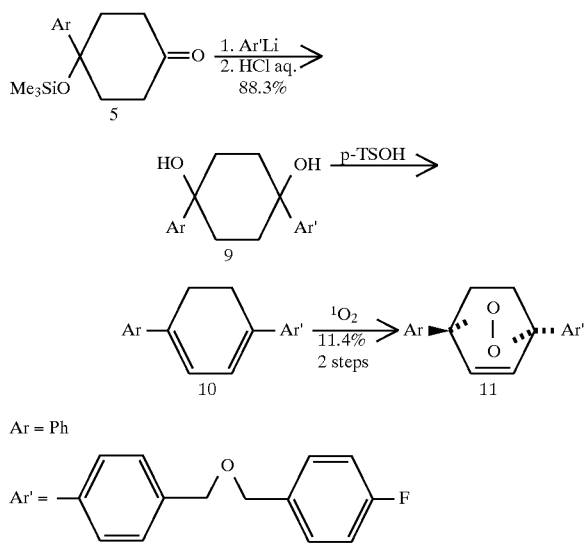

Ar = Ph

To a solution of 4-bromo-4'-fluorodibenzyl ether (0.875 g, 3.14 mmol) in 20 mL of dry ether at −78° C. was added tert-butyllithium (1.7M in pentane, 2.8 mL) via a syringe. After stirring for 30 minutes, a solution of ketone 5 (0.57 g, 2.18 mmol) in 5 mL of ether was added. The reaction mixture was further stirred at −78° C. while allowing the temperature to rise to r.t. for one hour. The reaction mixture was poured into 40 mL of cold saturated ammonium chloride water solution. The aqueous solution was extracted with ether (50 mL×3) and the combined organic solution was dried (MgSO$_2$), and evaporated. The residue was chromatographed on a silica gel column to give 0.94 g product which was directly dissolved in 10 mL of THF. To this THF solution was added 1 mL of 2N HCl and the reaction mixture was stirred at r.t. for 30 minutes. Usual workup and silica gel column chromatography gave diol 9 (0.78 g, yield 88.3%) in two steps. To a solution of diol 9 (120 mg) in 20 mL of benzene, was added p-toluenesulfonic acid 5 mg and the resulting mixture was refluxed 5 minutes while the water formed was removed by a dean-stark separator. The reaction mixture was cooled to r.t. quickly with a ice bath. Benzene was evaporated and the crude diene 10 was directly subjected to the next reaction. A solution of crude diene 10 in 30 mL of dry methylene chloride was irradiated with a medium pressure mercury lamp using methylene blue (5 mg) as a sensitizer for three hours at 0° C. while dry oxygen was bubbled into the reaction solution slowly. The reaction mixture was concentrated and the residue was chromatographed on a silica gel column to give peroxide product 11 (13.5 mg, yield 11.4%) in two steps. For compound 11: $^1$H NMR (400 MHz, CDCl$_3$) δ 7.54–7.49 (4H, m), 7.43–7.30 (7H, m), 7.05–7.00 (2H, m), 6.867 (1H, d, J=8.4 Hz), 6.842 (1H, d, J=8.4 Hz), 4.552 (2H, s), 4.513 (2H, s),, 2.68–2.58 (2H, m), 2.02–1.98 (2H, m); $^{13}$C NMR (100.6 MHz, CDCl$_3$)δ 162.31 (1 C, d, J=245.76 Hz), 139.40 (1 C, s), 138.89 (1 C, s), 138.42 (1 C, s), 136.58 (1 C, s), 136.46 (1 C, s), 133.83 (1 C, d, J=3.1 Hz), 129.51 (2 C, d, J=8.45 Hz), 128.57 (2 C, s), 128.447 (1 C, s), 127.90 (2 C, s), 126.26 (2 C, s), 126.11 (2 C, s), 115.256 (2 C, d, J=21.4 Hz), 78.39 (1 C, s), 71.705 (1 C, s), 71.55 (1 C, s), 29.55 (1 C, s), 29.50 (1 C, s).]]

2. Biological Activity of The Endoperoxides a. Antimalarial Activity

The protozoan Plasmodium falciparum is a causative agent of malaria, the single most critical infectious disease of mankind. The antimalarial activity of the endoperoxides was determined according to the method of Desjardins et al. (16) as modified by Milhous et al. (17). Briefly, the antimalarial activity of the endoperoxides was tested in a tritiated-hypoxanthine incorporation assay by determining the concentration of the test compound needed to inhibit 50% of the replication of *Plasmodium falciparum* (IC$_{50}$) in human red blood cells.

b. Activity Aganinst *Toxoplasma gondii*

*Toxoplasma gondii* is the causative agent of cerebral toxoplasmic encephalitis, an AIDS-related opportunistic infection. The biological activity of the endoperoxide JHU 2886 of the present invention was measured against *Toxoplasma gondii* cultured in L929 cells.

More specifically, the cytotoxicity of synthetic organic endoperoxide JHU 2886 was tested in L929 cells by measuring the viability and replication of exposed cells. The cytotoxicity of the compound to the cultured cells was measured using the MTT assay (Promega kit), according to the procedure of Carmichael et al. (18). MTT is an abbreviation for [3-(4,5-dimethylthiazol-2-yl)-2,5-dephenyltetrazolium bromide].

The inhibitory activity of the synthetic organic endoperoxide was tested by measuring the intracellular replication of *T. gondii* in infected L929 cells. The inhibition of the intracellular replication of *T. gondii* was determined using the uracil incorporation assay (20).

The results from these tests are shown in Table 1. More specifically, Table 1 shows the effect of a compound of the formula:

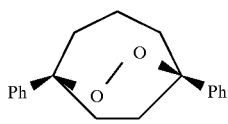

on the viability and replication of L929 cells and on the intracellular replication of *T. gondii*. This compound is referred to as JHU 2886 in Table 1. In this experiment atovaquone and artemisinin were used as positive controls. Atovaquone is a broad-spectrum anti-infective drug having antimalarial and antitoxoplasmosis activity (19).

As shown in Table 1, there was little toxicity seen after 24, 48 and 72 hours in L929 cells exposed to concentrations of JHU 2886 as high as 10 $\mu$M. There was some toxicity seen at concentrations of 50 $\mu$M. There was significant antiparasitic activity seen at 24 and 48 hours at all concentrations of JHU 2886 tested. There was significant activity seen at 72 hours for concentrations of 1 $\mu$M and above.

It is particularly noted that JHU 2886 has an excellent therapeutic index (ratio of activity to toxicity). At 1 $\mu$M, JHU 2886 has a therapeutic index of 70/0, whereas at the same concentration artimisinin has a therapeutic index of 76/10 (7.6), and atovaquone has a therapeutic index of only 95/17 (5.6). (Relevant entries shown in bold type in Table 1.) p Table 2 shows the structures of several organic endoperoxides of the present invention. The upper section shows seven saturated bicyclo (3,2,2) endoperoxides. The first two compounds are known while the following five are being disclosed for the first time. The far right column shows the concentration of the compound needed to inhibit 50% of the replication of *Plasmodium falciparum* ($IC_{50}$) in human red blood cells, as determined in the tritiated-hypoxanthine incorporation assay. Compounds of this formula wherein Ar is p-FCH$_2$Ph or p-HOCH$_2$Ph and X is CH$_2$ are also expected to be particularly useful.

The bottom section of Table 2 shows the structure of a known unsaturated endoperoxide. This compound is identical to the unsaturated seven carbon ring compound in Table 3. The $IC_{50}$ for this compound is given as 150 nM in both Table 2 and Table 3. The bottom section of Table 2 also reveals the $IC_{50}$ for the naturally-occurring artemisinin.

Table 3 shows the structures of several unsaturated organic endoperoxides of the present invention. The first three compounds are known while the following compound is being disclosed for the first time. Again, the far right column shows the concentration of the compound needed to inhibit 50% of the replication of *Plasmodium falciparum* ($IC_{50}$) in human red blood cells, as determined in the tritiated-hypoxanthine incorporation assay.

Tables 4 and 5 show the structures and antimalarial activities of unsaturated and saturated bicyclic [2.2.2] endoperoxides of the invention. Compounds of this formula wherein R and R' are identical are particularly preferred. It is expected that compounds wherein R and R' are selected from the groups

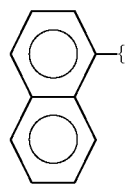

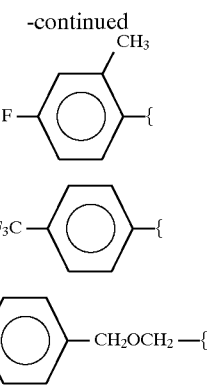

will be especially useful.

In addition, compounds of the structure shown in Table 5 in which R is

CH$_2$OH, CH$_2$F, CH$_2$OCH$_2$CONH$_2$, CH$_2$OP(OPh)$_2$,
$$\overset{O}{\underset{\|}{}}$$

$$CH_2OCN(CH_2CH_3)_2, \text{ and } CH_2OCH_2PhF\text{-}p$$
$$\overset{O}{\underset{\|}{}}$$

should be effective antimalarial/antiparasitic agents and are included in the invention.

Table 6 shows the structures and antimalarial activities of several saturated bicyclic [3.2.2] endoperoxides of the invention. In addition, compounds of the structure shown in Table 6 wherein R is CH$_2$F, and compounds of the structure

R—⬡—⬢—⬡—R where R is

F, CH$_2$OH, CH$_2$F, CH$_2$OP(OPh)$_2$,
$$\overset{O}{\underset{\|}{}}$$

CH$_2$OCN(CH$_2$CH$_3$)$_2$, and CH$_2$OCH$_2$PhF-p
$$\overset{O}{\underset{\|}{}}$$

are expected to be effective antimalarial/antiparasitic agents and are included in the invention.

It is considered that compounds with an $IC_{50}$ less than or equal to about 200 nM should be especially useful for practicing the invention, with compounds with an $IC_{50}$ of less than 100 nM being particularly preferred. However, the invention is not limited to such compounds, as compounds with higher $IC_{50}$'s will be useful if their toxicity is low.

While the invention has been described in connection with what is presently considered to be the most practical and preferred embodiments, it is to be understood that the invention is not to be limited to the disclosed embodiments, but on the contrary is intended to cover various modifications and equivalent arrangements included within the spirit and scope of the appended claims, including other anti-infective uses.

The following scientific articles and references have been cited throughout this application and the entire contents of each article or reference is hereby incorporated by reference.

SCIENTIFIC ARTICLES

1. Jing-Ming, J., et al., Acta Chim. Sinica 37:129 (1979).
2. Schmid, G., et al., J. Am. Chem. Soc. 105:624 (1983).
3. Qinghaosu Antimalaria Coordinating Research Group, Chinese Med. J. 92:811 (1979).
4. Jiang, J. -B., et al., Lancet 2:285 (1982).
5. Bruce-Chwatt, L. J., Brit. Med. J. 284:767 (1982).
6. Luo, X. D., et al., Med. Res. Rev. 7:29–52 (1987).
7. Klayman, D. L., Science 228:1049–1054 (1985).
8. Koch, H., Pharm. Int. 2:184–185 (1981).
9. Miyashi, T., et al., J. Am. Chem. Soc. 110:3676–3677 (1988).
10. Miyashi, T., et al., Pure & Appl. Chem. 62:1531–1538 (1990).
11. Takahashi, Y., et al., Tetrahedron Letters 35:3953–3956 (1994).
12. Kuhn, H. J., Diplomarbeit, Univ. Gottingen (1959).
13. Schenck, G. O., et al., Naturwissenschaften 41:374 (1954).
14. Rigaudy, J., et al., Tetrahedron Letters pp. 95–99 (1961).
15. Cope, A. C., et al., J. Am. Chem. Soc. 77:4939–4940 (1955).
16. Desjardins, R. E., et al., Antimicrob. Agents Chemother. 16:710–718 (1979).
17. Milhous, W. K., et al., Antimicrob. Agents Chemother. 27:525–530 (1985).
18. Carmichael, J., et al., Cancer Res. 47:936–942 (1987).
19. Hudson, A. T., Parasitology Today 9:66–68 (1993).
20. Fraser, D. C., et al., Biochem. Biophys. Res. Comm. 135:886–893 (1986).

TABLE 1

JUSTIFICATION OF SOME COMPOUNDS BASED ON THE VIABILITY AND REPLICATION OF L929 CELLS AND ON THE INTRACELLULAR REPLICATION OF T. gondii

| DRUG EXPERIMENT[1] | DOSE μM | 24 Hours Mean | S.C. | % of control | Score[2] | 48 Hours Mean | S.D. | % of control | Score[2] | 72 Hours Mean | S.D. | % of control | Score[2] |
|---|---|---|---|---|---|---|---|---|---|---|---|---|---|
| Atovaquone Toxicity | 0.0 | 0.113 | 0.008 | | | 0.213 | 0.009 | | | 0.438 | 0.014 | | |
| | 0.1 | 0.095 | 0.006 | 15.63 | 1 | 0.214 | 0.001 | 0.00 | 0 | 0.473 | 0.021 | 0.00 | 0 |
| | 1.0 | 0.093 | 0.003 | 17.40 | 1 | 0.211 | 0.008 | 1.09 | 1 | 0.464 | 0.033 | 0.00 | 0 |
| | 10.0 | 0.092 | 0.002 | 18.29 | 1 | 0.204 | 0.013 | 4.53 | 1 | 0.456 | 0.023 | 0.00 | 0 |
| | 50.0 | 0.089 | 0.10 | 21.24 | 2 | 0.106 | 0.009 | 50.16 | 3 | 0.161 | 0.005 | 63.24 | 3 |
| Atovaquone Activity | 0.0 | 14351 | 3588 | | | 17225 | 946 | | | 7234 | 1994 | | |
| | 0.1 | 3096 | 373 | 78.43 | 4 | 6865 | 512 | 60.15 | 3 | 2940 | 677 | 659.36 | 3 |
| | 1.0 | 693 | 98 | 95.17 | 5 | 729 | 90 | 95.77 | 5 | 1272 | 117 | 8242 | 4 |
| | 10.0 | 612 | 67 | 95.74 | 5 | 399 | 56 | 97.68 | 5 | 446 | 136 | 93.84 | 5 |
| | 50.0 | 1042 | 121 | 92.74 | 5 | 236 | 35 | 98.63 | 5 | 230 | 405 | 96.82 | 5 |
| Artemisinin Toxicity | 0.0 | 0.113 | 0.008 | | | 0.213 | 0.009 | | | 0.438 | 0.014 | | |
| | 0.1 | 0.103 | 0.007 | 8.56 | 1 | 0.213 | 0.009 | 0.00 | 0 | 0.460 | 0.015 | 0.00 | 0 |
| | 1.0 | 0.101 | 0.004 | 10.32 | 1 | 0.205 | 0.007 | 3.75 | 1 | 0.394 | 0.013 | 9.97 | 1 |
| | 10.0 | 0.104 | 0.003 | 7.67 | 1 | 0.195 | 0.009 | 8.44 | 1 | 0.354 | 0.014 | 19.18 | 1 |
| | 50.0 | 0.110 | 0.006 | 2.36 | 1 | 0.193 | 0.006 | 9.53 | 1 | 0.348 | 0.006 | 20.55 | 2 |
| Artemisinin Activity | 0.0 | 14351 | 3588 | | | 17225 | 946 | | | 7234 | 1994 | | |
| | 0.1 | 10106 | 2429 | 29.58 | 2 | 15440 | 1999 | 10.36 | 1 | 8253 | 3474 | −14.10 | 0 |
| | 1.0 | 3467 | 1028 | 75.84 | 4 | 6101 | 990 | 64.58 | 3 | 1976 | 1051 | 72.68 | 4 |
| | 10.0 | 3470 | 843 | 75.82 | 4 | 4225 | 327 | 75.47 | 4 | 783 | 368 | 89.17 | 4 |
| | 50.0 | 33322 | 810 | 76.85 | 4 | 4167 | 117 | 75.81 | 4 | 813 | 285 | 88.77 | 4 |
| JHU 2886 Toxicity | 0.0 | 0.129 | 0.005 | | | 0.211 | 0.006 | | | 0.439 | 0.014 | | |
| | 0.1 | 0.129 | 0.005 | 0.26 | 1 | 0.227 | 0.003 | 0.00 | 0 | 0.479 | 0.026 | 0.00 | 0 |
| | 1.0 | 0.133 | 0.005 | 0.00 | 0 | 0.219 | 0.009 | 0.00 | 0 | 0.460 | 0.008 | 0.00 | 0 |
| | 10.0 | 0.130 | 0.005 | 0.00 | 0 | 0.217 | 0.008 | 0.00 | 0 | 0.448 | 0.023 | 0.00 | 0 |
| | 50.0 | 0.089 | 0.005 | 31.19 | 2 | 0.147 | 0.008 | 30.38 | 2 | 0.275 | 0.005 | 37.43 | 2 |
| JHU 2886 Activity | 0.00 | 8782 | 1629 | | | 15819 | 1074 | | | 7166 | 784 | | |
| | 0.1 | 6079 | 91 | 3078 | 2 | 14841 | 2301 | 6.18 | 1 | 6934 | 1197 | 3.24 | 1 |
| | 1.0 | 2668 | 386 | 69.62 | 3 | 12880 | 1946 | 18.58 | 1 | 6219 | 2202 | 13.21 | 1 |
| | 10.0 | 1967 | 259 | 77.60 | 4 | 4428 | 780 | 72.01 | 4 | 1321 | 244 | 81.57 | 4 |
| | 50.0 | 2104 | 478 | 76.04 | 4 | 1808 | 169 | 88.57 | 4 | 1252 | 217 | 82.53 | 4 |

[1]The cytotoxicity of each compound for the cultured cells was measured using the MTT assay (Promega kit) and inhibition of the intracellular replication of T. gondii was determined using the uracil incorporation assay.
[2]The extent of toxicity or activity (in percent of control) was scored based on the following criterion:
0 = No reduction
1 = ≦20%
2 = >20%–≦40%
3 = >40%–≦70%
4 = >70%–≦90%
5 = >90%

TABLE 2

ANTIMALARIAL ACTIVITY COMPARED TO
THE POTENT ANTIMALARIAL ARTEMISININ

| KNOWN | Ar | X | IC$_{50}$ (nM) |
|---|---|---|---|
| Yes | Ph | CH$_2$ | 89 |
| Yes | p-MeOPh | CH$_2$ | 62 |
|  | p-FPh | CH$_2$ | 38 |
|  | Ph | α-HC—⟨C$_6$H$_4$⟩—OMe | 180 |
|  | Ph | β-HC—⟨C$_6$H$_4$⟩—OMe | 410 |
|  | Ph | SO$_2$ | >1000 |
|  | Ph | C(CH$_3$)$_2$ | >1000 |
|  | Ph | C(cyclohexyl) | >1000 |
| Yes | Ph, Ph (unsaturated) |  | 150 |
| Yes | Artemisinin |  | 11 |

TABLE 3

ANTIMALARIAL ACTIVITY

| KNOWN | n | Ring Size | IC$_{50}$ (nM) |
|---|---|---|---|
| Yes | 1 | 5 | 650 |
| Yes | 2 | 6 | 150 |
| Yes | 3 | 7 | 150 |
|  | 4 | 8 | 410 |

TABLE 4

Unsaturated Bicyclic [2.2.2] Endoperoxides

| R | R' | Antimalarial Activity IC$_{50}$ (nM) (*P. falciparum* NF54 Parasites in vitro) |
|---|---|---|
| H | H | 180 |
| Me | Me | 140 |
| F | F | 70 |
| H | F | 71 |

TABLE 4-continued

Unsaturated Bicyclic [2.2.2] Endoperoxides

| R | R' | Antimalarial Activity IC$_{50}$ (nM) (*P. falciparum* NF54 Parasites in vitro) |
|---|---|---|
| H | p-PhCH$_2$OCH$_2$PhF-p | 210 |
| p-CF$_3$Ph | p-CF$_3$Ph | 110 |
| Artemisinin |  | 11 |

TABLE 5

Saturated Bicyclic [2.2.2] Endoperoxides

| R | Antimalarial Activity IC$_{50}$ (nM) (*P. falciparum* NF 54 Parasites in vitro) |
|---|---|
| H | 210 |
| CF$_3$ | 82 |
| F | 63 |
| Artemisinin | 11 |

TABLE 6

Saturated Bicyclic [3.2.2] Endoperoxides

| R | Antimalarial Activity IC$_{50}$ (nM) (*P. falciparum* NF54 Parasites in vitro) |
|---|---|
| H | 89 |
| OH | >2500 |
| OSiMe$_2$Bu-t | 290 |
| CH$_2$OSiMe$_2$Bu-t | 99 |
| CH$_2$OH | 81 |
| F | 42 |

What is claimed is:

1. A compound of the formula:

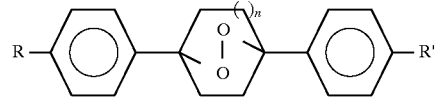

wherein n is 1 or 2 and R and R' are independently selected from the group consisting of H, OH, OSiMe$_2$Bu-t, CH$_2$OSiMe$_2$Bu-t, CH$_2$OH, CH$_2$F, CH$_2$OCH$_2$CONH$_2$ and F, and wherein R and R' are not both H.

2. The compound of claim 1 wherein n is 2.

3. The compound of claim 2 wherein and R and R' are identical.

4. The compound of claim 3 wherein R and R' are selected from the group consisting of H, CH$_2$OH, CH$_2$F, and F.

5. The compound of claim 2 wherein R is H and R' is selected from the group consisting of OH, OSiMe$_2$Bu-t, CH$_2$OSiMe$_2$Bu-t, CH$_2$OH, CH$_2$F, and F.

6. The compound of claim 1 wherein n is 1.

7. The compound of claim 6 wherein R and R' are selected from the group consisting of H, CH$_2$OH, CH$_2$F, F, and CH$_2$OCH$_2$CONH$_2$.

8. A compound of the formula:

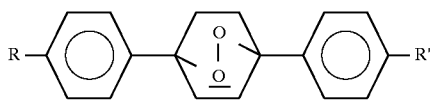

wherein R and R' are independently selected from the group consisting of H, CH₃, F and p-PhCH₂OCH₂PhF-p, and wherein R and R' are not both H.

9. The compound of claim 8 wherein R is H.

10. The compound of claim 8 wherein R and R' are identical.

11. A method for treating a parasitic infection comprising the step of administering to an individual afflicted with malaria an organic endoperoxide represented by the formula:

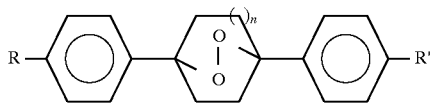

wherein n is 1 or 2 and R and R' are independently selected from the group consisting of H, OH, OSiMe₂Bu-t, CH₂OSiMe₂Bu-t, CH₂OH, CH₂F, CH₂OCH₂CONH₂ and F, and wherein R and R' are not both H.

12. The method of claim 11 wherein the parasitic infection is malaria or cerebral toxoplasmic encephalitis.

13. The method of claim 12 wherein n is 2.

14. The method of claim 13 wherein and R and R' are identical.

15. The method of claim 14 wherein R and R' are selected from the group consisting of H, CH₂OH, CH₂F, and F.

16. The method of claim 13 wherein R is H and R' is selected from the group consisting of OH, OSiMe₂Bu-t, CH₂OSiMe₂Bu-t, CH₂OH, CH₂F, and F.

17. The method of claim 12 wherein n is 1.

18. The method of claim 17 wherein R and R' are selected from the group consisting of H, CH₂OH, CH₂F, F, and CH₂OCH₂CONH₂.

19. A method for treating a parasitic infection comprising the step of administering to an individual afflicted with malaria an organic endoperoxide represented by the formula:

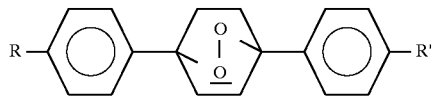

wherein R and R' are independently selected from the group consisting of H, CH₃, F and p-PhCH₂OCH₂PhF-p, and wherein R and R' are not both H.

20. The method of claim 19 wherein the parasitic infection is malaria or cerebral toxoplasmic encephalitis.

21. The method of claim 20 wherein R is H.

22. The method of claim 20 wherein R and R' are identical.

* * * * *